United States Patent
Cha et al.

(10) Patent No.: US 9,657,273 B2
(45) Date of Patent: May 23, 2017

(54) METHOD FOR SUPPRESSING TERATOMA FORMATION VIA SELECTIVE CELL DEATH INDUCTION IN UNDIFFERENTIATED HUMAN-INDUCED PLURIPOTENT STEM CELLS

(71) Applicant: Industry-University Cooperation Foundation Sogang University, Seoul (KR)

(72) Inventors: Hyuk Jin Cha, Seoul (KR); Kwang Soo Kim, Lexington, MA (US)

(73) Assignee: Industry-University Cooperation Foundation Sogang University, Seoul (KR)

( * ) Notice: Subject to any disclaimer, the term of this patent is extended or adjusted under 35 U.S.C. 154(b) by 88 days.

(21) Appl. No.: 14/434,873

(22) PCT Filed: Oct. 11, 2013

(86) PCT No.: PCT/KR2013/009111
§ 371 (c)(1),
(2) Date: Apr. 10, 2015

(87) PCT Pub. No.: WO2014/058274
PCT Pub. Date: Apr. 17, 2014

(65) Prior Publication Data
US 2016/0002604 A1    Jan. 7, 2016

(30) Foreign Application Priority Data
Oct. 12, 2012   (KR) .................. 10-2012-0113636

(51) Int. Cl.
*C12N 5/00* (2006.01)
*C12N 5/074* (2010.01)
*C07D 311/30* (2006.01)
*C07D 311/22* (2006.01)
*C07D 403/06* (2006.01)

(52) U.S. Cl.
CPC .......... *C12N 5/0696* (2013.01); *C07D 311/22* (2013.01); *C07D 311/30* (2013.01); *C07D 403/06* (2013.01); *C12N 2500/76* (2013.01); *C12N 2502/1347* (2013.01); *C12N 2506/45* (2013.01)

(58) Field of Classification Search
CPC .. C12N 5/0696; C07D 311/22; C07D 311/30; C07D 403/06
See application file for complete search history.

(56) References Cited

FOREIGN PATENT DOCUMENTS

| KR | 100717724 B1 | 5/2007 |
|----|--------------|--------|
| KR | 1020110042426 A | 4/2011 |

OTHER PUBLICATIONS

Wang et al. PNAS 104(11):4449-4454, 2007.*
Nakahara et al. Cancer Research 67(17):8014-21, 2007.*
Lee et al. PNAS 110(35):E3281-3290, published online: Aug. 5, 2013.*
Sasaki et al., "Quercetin-induced PC12 cell death accompanied by caspase-mediated DNA fragmentation," Biol Pharm Bull. 30(4):682-6 (2007).
Shen et al., "Differential apoptosis-inducing effect of quercetin and its glycosides in human promyeloleukemic HL-60 cells by alternative activation of the caspase 3 cascade," J Cell Biochem. 89(5):1044-55 (2003).
Yamanaka et al., "Antitumor activity of YM155, a selective small-molecule survivin suppressant, alone and in combination with docetaxel in human malignant melanoma models," Clin Cancer Res. 17(16):5423-31 (2011).
International Search Report for International Patent Application No. PCT/KR2013/009111, dated Nov. 12, 2013 (2 pages).

\* cited by examiner

*Primary Examiner* — Marcia S Noble
(74) *Attorney, Agent, or Firm* — Clark & Elbing LLP; Susan M. Michaud

(57) ABSTRACT

The present invention relates to a method for preparing differentiated cells derived from induced pluripotent stem cell, wherein undifferentiated induced pluripotent stem cells (iPS) are removed, the method comprising steps of: (a) preparing a cell sample including undifferentiated induced pluripotent stem cells and differentiated cells by differentiating induced pluripotent stem cells; and (b) causing selective apoptosis of the undifferentiated induced pluripotent stem cells by treating the resultant in step (a) with quercetin of Formula 1 below or with YM-155 of Formula 2 below. According to the present invention, the present invention makes it possible to effectively selectively cause apoptosis only of undifferentiated induced pluripotent stem cells by causing induced pluripotent stem cells to differentiate into specific differentiated cells and then carrying out culturing in a differentiating culture medium comprising quercetin or YM-155, and, in the induced pluripotent stem cell differentiation method according to the present invention, only undifferentiated induced pluripotent stem cells that are a cause of teratoma formation are selectively caused to die, and thus differentiated differentiating cells are completely unaffected. In other words, the invention can be expected to ensure safety as the possibility of tumor formation during clinical use as a cell therapeutic agent is eliminated since the survival and functioning of the differentiated cells is maintained unchanged.

4 Claims, 16 Drawing Sheets

METHOD FOR SUPPRESSING TERATOMA FORMATION VIA SELECTIVE CELL DEATH INDUCTION IN UNDIFFERENTIATED HUMAN-INDUCED PLURIPOTENT STEM CELLS

TECHNICAL FIELD

The present invention was accomplished according to project number 2011-0030832 under the Ministry of Education and Science Technology (MEST), Republic of Korea. The special agency of R&D management for the above project is National Research Foundation of Korea, the name of the research program is "Basic Research Program-Leading Research Center Rearing Project (Science and Engineering Fields)—Scientific Research Center", the research project title is "Research on Signaling for Maintaining Genomic Stability of Stem Cells", the Supervising Organization is Sogang University, and the research period is between Sep. 7, 2011 and Aug. 31, 2018.

This application claims priority and the benefit of Korean Patent Application No. 10-2012-0113636, filed on Oct. 12, 2012, in the Korean Intellectual Property Office, the disclosure of which is incorporated herein in its entirety by reference.

The present invention relates to a method for suppressing teratoma formation via selective cell death induction in undifferentiated human induced pluripotent stem cells.

BACKGROUND ART

Human induced pluripotent stem cells have pluripotency to be differentiated into triploblastic (endoderm, mesoderm, and ectoderm) cells constituting the human body and the characteristic of self-renewal capable of continuously undergoing cell divisions. Therefore, various studies have been performed on their differentiation into cells necessary for regenerative medicine, e.g., nerve cells, liver cells, blood cells, etc. In order to obtain differentiated cells from human induced pluripotent stem cells, a Fluorescent Activated Cells Sorter (FACS) or a Magnetic Cell Sorting (MACS) may be used. The FACS method includes inducing differentiation of human induced pluripotent stem cells into specific cells and separating the cells marked by antibodies of specific surface markers of the differentiated cells through FACS to obtain only the differentiated cells (Fukuda, H et al., "Fluorescence-Activated Cell Sorting-Based Purification of Embryonic Stem Cell-Derived Neural Precursors Averts Tumor Formation After Transplantation" Stem Cells (2006)(24.3: 763-771)). In the MACS method, the differentiated cells are obtained using antibody markers and magnetism (David, R et al., "Magnetic Cell Sorting Purification of Differentiated Embryonic Stem Cells Stably Expressing Truncated Human Cd4 as Surface Marker" Stem Cells (2005) (23.4: 77-82)). The MACS method has an advantage in that it can get rid of the danger of exposing cells to laser being applied during the separation using the FACS.

However, both FACS and MACS methods cannot exclude the possibility of the mixed presence of undifferentiated induced pluripotent stem cells, and thus there is a technical limitation in separating only the differentiated cells with 100% purity. In particular, it is possible that undifferentiated cells may be mixed in the differentiated cells derived from induced pluripotent stem cells. Accordingly, in the development of a cell therapeutic agent using induced pluripotent stem cells, there is a continuing controversy regarding the danger of formation of teratoma, a tumor derived from undifferentiated pluripotent stem cells. Therefore, there is a demand in the art on the development of a technology capable of selectively removing undifferentiated cells having the potential danger of teratoma, without affecting the differentiated cells.

Numerous journal articles and patent documents are referred to herein over the entire specification and indicated as referred to. The disclosure of the cited journal articles and the patent documents are incorporated herein in their entirety by reference to further elucidate the level of the technologies to which the present invention belongs and the details of the present invention.

DISCLOSURE OF THE INVENTION

Technical Problem

The present inventors have made intensive efforts to develop a method for obtaining pure differentiated cells from induced pluripotent stem cells, and in particular, a method for obtaining only the pure differentiated cells by removing the possibility of a tumor formation by the undifferentiated induced pluripotent stem cells causing teratoma formation. As a result, the present inventors discovered that when induced pluripotent stem cells were treated with quercetin or YM-155, which suppresses the expression of Survivin, an anti-cell death factor, only the undifferentiated induced pluripotent stem cells were effectively and selectively killed without affecting the differentiated cells at all, thereby completing the present invention.

Accordingly, one object of the present invention is to provide a method for preparing differentiated cells derived from induced pluripotent stem cells (iPS), wherein undifferentiated induced pluripotent stem cells are removed therefrom.

Another object of the present invention is to provide a cell composition wherein the undifferentiated induced pluripotent stem cells (iPS) are removed.

Another object of the present invention is to provide a composition for selective cell death of undifferentiated induced pluripotent stem cells.

The present invention have other features and advantages which will be apparent from or are set forth in more detail in the accompanying drawings, which are incorporated herein, and the following Detailed Description of the Invention, which together serve to explain certain principles of the present invention.

Technical Solution

In an aspect of the present invention, there is provided a method for preparing differentiated cells derived from induced pluripotent stem cells, wherein undifferentiated induced pluripotent stem cells (iPS) are removed, including the steps of:

(a) preparing a cell sample including undifferentiated induced pluripotent stem cells and differentiated cells by differentiating the induced pluripotent stem cells; and (b) causing selective death of the undifferentiated induced pluripotent stem cells by treating the resultant in step (a) with quercetin or YM-155.

The present inventors have made intensive efforts to develop a method for obtaining pure differentiated cells from induced pluripotent stem cells, and in particular, a method for obtaining only the pure differentiated cells by removing the possibility of a tumor formation by the undifferentiated induced pluripotent stem cells causing teratoma formation. As a result, the present inventors discovered that when induced pluripotent stem cells were treated with quercetin or YM-155, which suppresses the expression of Survivin, an anti-cell death factor, only the undifferentiated induced pluripotent stem cells were effectively and selectively killed without affecting the differentiated cells at all, thereby completing the present invention.

The method for preparing differentiated cells derived from induced pluripotent stem cells, wherein undifferentiated induced pluripotent stem cell (iPS) are removed, may be explained in greater details according to each respective step as set forth herein below:

Step (a): Preparation of a Cell Sample Including Undifferentiated Induced Pluripotent Stem Cells and Differentiated Cells by Differentiating Induced Pluripotent Stem Cells According to the present invention, first, the induced pluripotent stem cells are differentiated to prepare a cell sample including undifferentiated induced pluripotent stem cells and differentiated cells.

The above cell sample may be prepared in various ways. For example, the above cell sample is a result of the differentiation of the induced pluripotent stem cells (e.g., differentiation into smooth muscle cells). Generally, the product resulted from the differentiation of the induced pluripotent stem cells does not necessarily include only the differentiated cells but forms an heterogeneous population including a small amount of undifferentiated induced pluripotent stem cells. Accordingly, in order to use the differentiated product as a cell therapeutic agent, it is necessary to completely remove the undifferentiated induced pluripotent stem cells.

The term "induced pluripotent stem cells" as used herein refers to pluripotent stem cells artificially derived from non-pluripotent cells (e.g., somatic cells) by insertion of a specific gene. The induced pluripotent stem cells are considered the same as pluripotent stem cells (e.g., embryonic stem cells) in that the induced pluripotent stem cells have the characteristics of expression of stem cell genes and proteins, methylation of chromosomes, doubling time, embryoid body formation, teratoma formation, viable chimera formation, hybridization and differentiation.

The term "differentiated cells" as used herein refer to cells which were differentiated from stem cells into specific cells triggered by a specific differentiation stimulus.

According to a preferred embodiment of the present invention, the induced pluripotent stem cells used in the present invention are derived from humans, cattle, horses, goats, sheep, dogs, cats, mice, rats, or birds, and preferably are human induced pluripotent stem cells.

The induced pluripotent stem cells refer to pluripotent cells which induced the pluripotency of embryonic stem cells by introducing 3 or 4 different kinds of genes, and these induced pluripotent stem cells may be easily constructed via various methods known in the art (Takahashi K, Yamanaka S (August 2006). "Induction of pluripotent stem cells from mouse embryonic and adult fibroblast cultures by defined factors". *Cell* 126(4):663-76).

For example, induced pluripotent stem cells may be obtained by culturing in a suitable medium such as Dulbecco's Modified Eagle's Medium (DMEM) including, as supporting cells, mouse embryonic fibroblasts (MEFs) treated with mitomycin-C to inhibit proliferation, and supplemented with fetal bovine serum (FBS), β-mercaptoethanol and non-essential amino acids, followed by subculturing in a Knockout-DMEM supplemented with a serum replacement, β-mercaptoethanol, non-essential amino acids, and bFGF2. As a known induced pluripotent stem cell line, SES-8 (Tae-Hee Lee et al., "Functional Recapitulation of Smooth Muscle Cells Via Induced Pluripotent Stem Cells From Human Aortic Smooth Muscle Cells" Circulation Research (2010) (106:120-128)) or the like may be used, but is not limited thereto.

The induced pluripotent stem cells used in the method of the present invention may be autologous or allogenic to the subject, from which the pluripotent stem cells were derived, and preferably autologous. The autologous induced pluripotent stem cells are separated from the tissues of the subject itself, and cultured to be prepared therefrom.

In the method of the present invention, the cell sample treated with quercetin or YM-155 includes any product obtained by differentiating the induced pluripotent stem cells.

For example, a cell population obtained by differentiating the induced pluripotent stem cells into specific cells, and a cell population obtained by differentiating embryoid bodies derived from the induced pluripotent stem cells, etc., may be used in the present invention.

The term "embryoid body" as used herein refers to a cell mass formed by natural differentiation of embryonic stem cells, and is an cell aggregate capable of being differentiated into three germ layers of endoderm, mesoderm, and ectoderm, and the thus obtained embryoid body may be maintained in a suitable medium. Formation of embryoid body from the induced pluripotent stem cells may be performed using various methods known in the art. For example, embryoid body may be formed using a method disclosed by Kim J et al., "Effective Isolation and Culture of Endothelial Cells in Embryoid Body Differentiated from Human Embryonic Stem Cells", Stem cell and Development (2007) (16: 269-280), by culturing the induced pluripotent stem cells in a DMEM/F12 medium containing blood serum (or a blood serum replacement), L-glutamine, non-essential amino acids, and β-mercaptoethanol. Additionally, embryoid body may be formed by separating colonies of the induced pluripotent stem cells from the co-cultured neighboring supporting cells (MEF), followed by culturing in a medium with no addition of bFGF2, i.e., a Knockout-DMEM supplemented with a blood serum replacement, β-mercaptoethanol, non-essential amino acids, and bFGF2 via suspending culture.

In the method of the present invention, matrix cells of various compositions may be contained in a medium depending on the type of cells to be obtained, and the differentiation of the embryoid body may be performed according to a known method. For example, as disclosed by Cho S W et al., "Improvement of postnatal neovascularization by human embryonic stem cell derived endothelial-like cell transplantation in a mouse model of hindlimb ischemia", Circulation (2007)(20; 116(21):2409-19), when the embryoid body derived from the induced pluripotent stem cells are differentiated into endothelial cells, the embryoid body may be obtained via suspending culture in a suitable medium (e.g., a DMEM/F12 medium added with 10% fetal bovine serum (FBS) and penicillin-streptomycin) for about 9 days. The thus obtained embryoid body may be obtained by separating the central part of the embryoid body by applying a physical force, for example using a pipette, and the central part of the human embryoid body separated therefrom may be cultured in a medium for the stem cell differentiation (e.g., EGM-2), but is not limited thereto.

Step (b): Selective Cell Death of Undifferentiated Induced Pluripotent Stem Cells by Treating the Product of Step (a) with Quercetin or YM-155

Then, in order to selectively remove the undifferentiated induced pluripotent stem cells, the product of Step (a) is treated with quercetin or YM-155. As a result, the viability and functions of the differentiated cells are maintained without being affected at all, and only the undifferentiated induced pluripotent stem cells are selectively killed.

The term "depletion or removal" as used herein, being used while describing the undifferentiated induced pluripotent stem cells, means that the undifferentiated induced pluripotent stem cells are substantially removed from heterogeneous cell population and thus teratoma is not formed. For example, the term "removal" used herein means that, in a sample where the method of the present invention is used, the amount of the undifferentiated induced pluripotent stem cells is less than 1%, preferably less than 0.5%, more preferably less than 0.1%, and most preferably substantially no amount. The term "%" used herein refers to a percentage based on cell count.

In the present invention, cell death refers to apoptosis, unless stated otherwise. Apoptosis is a programmed cell death (PCD) occurring in a multicelled specimen (Alberts, Bruce et al., (2008). "Chapter 18 Apoptosis: Programmed Cell Death Eliminates Unwanted Cells". Molecular Biology of the Cell ($5^{th}$ ed.), Garland Science. p. 1115). The biochemical phenomenon of apoptosis changes the shape of cells resulting to death. The above changes includes air bubble formation, cell contraction, nuclear spallation, chromosome condensation and chromosomal DNA spallation. Unlike cell necrosis, the apoptotic body produced by apoptosis is released out of the cell, and surrounded by phagocytic cells and removed before it damages the cell.

Quercetin, used in the present invention, is a chemical inhibitor of Survivin, an anti-apoptosis factor, whose chemical name is 2-(3,4-dihydroxyphenyl)-3,5,7-trihydroxy-4H-chromen-4-one, having a structure of Formula 1 below.

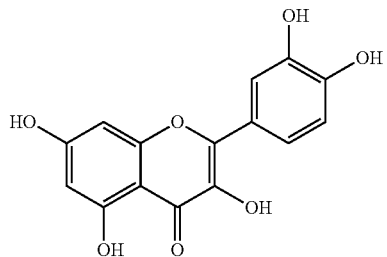

Formula 1

YM-155, used in the present invention, is a chemical inhibitor of Survivin, an anti-apoptosis factor, whose chemical name is 4,9-Dihydro-1-(2-methoxyethyl)-2-methyl-4,9-dioxo-3-(2-pyrazinylmethyl)-1H-naphtho[2,3-d]imidazolium bromide, having a structure of Formula 2 below.

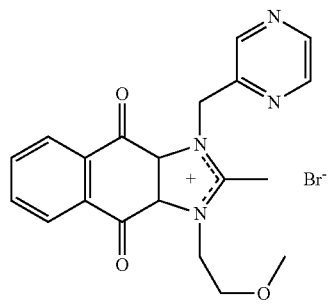

Formula 2

According to a preferable embodiment of the present invention, the concentration of quercetin is preferably in the range of 20 μM to 100 μM, more preferably 30 μM to 90 μM, even more preferably 40 μM to 80 μM, and most preferably 50 μM.

According to a preferable embodiment of the present invention, the concentration of YM-155 is preferably in the range of 2 nM to 80 nM, more preferably 5 nM to 70 nM, even more preferably 10 nM to 60 nM, and most preferably 10 nM to 50 μM.

The culture period for step (b) of the present invention is not particularly limited, but is preferably in the range of about 5 hours to about 100 hours, more preferably about 10 hours to about 50 hours, even more preferably about 15 hours to about 30 hours, and most preferably about 24 hours.

In another aspect of the present invention, there is provided a cell composition, wherein the undifferentiated induced pluripotent stem cells are removed according to the method of the present invention.

Since the composition of the present invention is prepared according to the method of the present invention described above, the description commonly shared between them is omitted in order to avoid excess complexity of the present specification.

The cell composition, wherein the undifferentiated induced pluripotent stem cells are removed, according to the method of the present invention, has various applicability, and in particular, may be used as a cell therapeutic agent.

For example, in the case of the product differentiated into muscle cells, wherein the undifferentiated induced pluripotent stem cells are removed, the cell composition may be used as an excellent supply source for cell therapy of muscle-related diseases including muscle-damaged diseases such as muscular dystrophy, muscular atrophy, myositis, polymyositis, peripheral vascular disease and fibrosis; neuromuscular diseases, muscular arthritis, degenerative muscular diseases, and ischemic muscular diseases, etc., but is not limited thereto.

Additionally, for example, in the case of the product differentiated into nerve cells, wherein the undifferentiated induced pluripotent stem cells are removed, the cell composition may be used as an excellent supply source for cell therapy of neurological diseases including stroke, traumatic brain injury, cerebral palsy, epilepsy, Alzheimer's disease, multiple sclerosis, Parkinson's disease, spinal cord injury disease, dementia, hepatic encephalopathy and hypoxia, demyelinating disease, Huntington's disease, amyotrophic lateral sclerosis, degenerative diseases and ischemic diseases, etc., but is not limited thereto.

In another aspect of the present invention, there is provided a composition for selective cell death of the undifferentiated induced pluripotent stem cells, which includes quercetin or YM-155.

Since the composition of the present invention includes quercetin or YM-155 used according to the method of the present invention described above, the description commonly shared between them is omitted in order to avoid excess complexity of the present specification.

Advantageous Effects

The constitutional features and advantages of the present invention may be summarized as follow:

(a) The present invention may effectively cause selective apoptosis of only the undifferentiated induce pluripotent stem cells, by differentiating the induced pluripotent stem cells into specific differentiated cells, followed by culturing the specific differentiated cells in a medium for differentiation containing quercetin or YM-155.

(b) The method of differentiating induced pluripotent stem cells according to the present invention causes selective apoptosis of only the undifferentiated induced pluripotent stem cells and does not affect the differentiated cells at all. In other words, because the viability and functions of the differentiated cells are maintained unchanged, it is expected to ensure safety by removing the possibility of tumor formation during clinical use as a cell therapeutic agent.

BRIEF DESCRIPTION OF THE DRAWINGS

FIG. 4b shows the results of PAS staining and H&E staining of the secretory epithelium and neural rosette structure, respectively, in order to confirm the teratoma formation in FIG. 4a.

FIG. 7b is a graph showing the results of interior calcium concentrations measured in FIG. 7a.

MODE FOR CARRYING OUT THE INVENTION

Figure 1A:
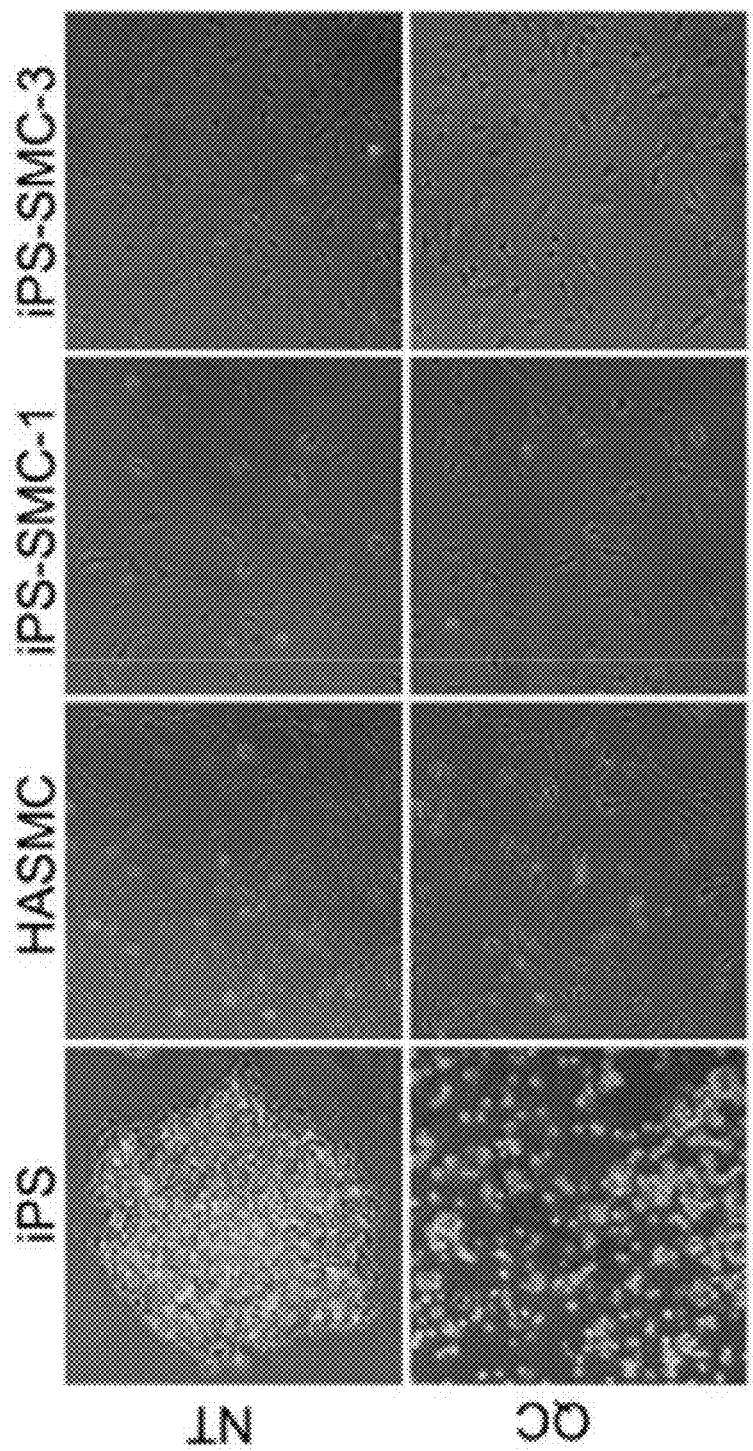
FIG. 1a shows the images of the degree of apoptosis in an apoptosis-specific cell type of human induced pluripotent stem cells (iPS) derived from human aortic smooth muscle cells (HASMC), HASMC, smooth muscle cell no. 1 differentiated-derived from iPS (iPS-SMC-1), and smooth muscle cell no. 3 differentiated-derived from iPS (iPS-SMC-3) observed under microscope, after treating them with 50 μM quercetin, respectively, for 24 hours. As a result, the human induced pluripotent stem cells treated with quercetin exhibited a distinct apoptosis-specific cell phenotype.

Hereinafter, the present invention will be described in greater details with reference to the accompanying examples. However, these examples disclosed herein are only for illustrative purposes of the present invention, and it shall be obvious to a skilled person in the art that they should not be construed as limiting the scope of the present invention.

EXAMPLES

Materials and Methods
Reagents

Quercetin (Cat # Q0125) was purchased from Sigma-Aldrich (St. Louis, Mo., USA), and YM-155 (Cat # S1130) was purchased from Selleck Chemicals.
Culturing and Differentiation of Human Induced Pluripotent Stem Cells (iPS)

Human induced pluripotent stem cells (iPS) derived from human aortic smooth muscle cells (HASMC) was subcultured in an ESC medium (DMEM/F/12 supplemented with a 20% KnockOut™ serum replacement, 0.1% gentamycin, 1% non-essential amino acids, 0.1% β-mercaptoethanol and 4 ng/ml bFGF) containing mouse embryonic fibroblasts (MEF) treated with mitomycin-C as supporting cells Lee, T. H., et al., (2010). Functional recapitulation of smooth muscle cells via induced pluripotent stem cells from human aortic smooth muscle cells. Circ Res 106, 120-128).

For the pretreatment of quercetin and YM-155 of the present invention, iPS was cultured in a matrigel-coated 60 mm dish containing mIeSR™1 medium (29106, Stem Cell Technology) to induce them into smooth muscle cells (SMC).
Culturing of Human Aortic Smooth Muscle Cells (HASMC) and Human Induced Pluripotent Stem Cells-Derived Differentiated Cells (iPS-SMC)

Human aortic smooth muscle cells (HASMC) and human induced pluripotent stem cells-derived differentiated cells, i.e., human induced pluripotent stem cells-derived smooth muscle cells (iPS-SMC) were cultured in an SMCM medium (ScienCell research laboratories, cat #1101) as described in the reference (Lee et al., 2010).
Immunoblotting and Immuno Fluorescence Cytochemistry (IFC)

The antibodies used in the immunoblotting assay and anti-PARP1 (SC-7150) and anti-β-actin (SC-47778) were purchased from Santa Cruz Biotech Inc. (CA, USA). Additionally, anti-caspase-9 (Cat#9502) and anti-cleaved caspase-3 (Cat#9661) purchased from Cell Signaling Technology (Danvers, Mass., USA).

As the first antibody used in IFA was anti-α-smooth muscle actin (α-SMA) (Dako Inc, Carpinteria, Calif.). Images were obtained using Axioscope A1 microscope (Carl Zeiss) and analyzed.

Real Time PCR
RNA extraction and cDNA synthesis were performed according to a general protocol (VanGuilder H D, et al (2008). "Twenty-five years of quantitative PCR for gene expression analysis". Biotechniques 44 (5): 619-626).

The gene-specific primer sequences used in the Examples of the present invention are as follows:

β-actin: 5'-GTCCTCTCCCAAGTCCACAC-3', (SEQ ID NO: 1)
5'-GGGAGACCAAAAGCCTTCAT-3' (SEQ ID NO:2)

α-SMA: 5'-AGAACATGGCATCATCACCA-3', (SEQ ID NO:3)
5'-TACATGGCTGGGACATTGAA-3'. (SEQ ID NO:4)

FACS Assay
In all FACS assays were used FACS Calibur™ (BD Biosciences) and CellQuest. Cells were stained using PE Annexin V Apoptosis Detection Kit I (BD Pharmingen™) according to the protocol described in the envelope of the product.
Teratoma Formation and Immunohistochemistry Since the differentiated cells lack of teratoma forming ability, in order to confirm the inhibitory effect of quercetin or YM-155 against teratoma formation, a teratoma forming experiment was performed by creating a condition including cells in an undifferentiated state. That is, cells (about $5 \times 10^6$ cells), where the embryoid body (EB) formed from iPS was treated with quercetin (100 μM) or YM-155 (10 nM), or untreated cells (about $5 \times 10^6$ cells) obtained were injected into testis of an NOD/SCID mouse (Charles River Laboratories, Yokohama, Japan) thereby forming teratoma. 10 weeks after the injection, the xenografted cells (xenograft mass) were obtained and fixed in 4% PFA for 2 weeks, and embedded in paraffin using Tissue-Tek VIP embedding machine (Miles Scientific, Naperville, Ill.) and Thermo Shandon Histocenter2 (Thermo Fisher Scientific, Waltham, Mass.). The thus prepared paraffin block was prepared into slices (2 μm thick) using a Leica RN2065 microtome (Leica, Wetzlar, Germany). In order to confirm teratoma formation, the slices were stained with Hematoxylin and eosin stain (H&E) and PAS (Periodic-Acid-Schiff), and analyzed by an experienced pathologist.

All the experiments of the present invention were approved by the Institutional Animal Care and Use Committee of CHA University, and all the procedures of the present invention were performed according to the 'Guidelines for the Care and Use of Laboratory Animals' published by the U.S. NIH (NIH publication no. 85-23, revised 1996).
Measurement of Intracellular Calcium ($Ca^{2+}$)

Figure 1B:
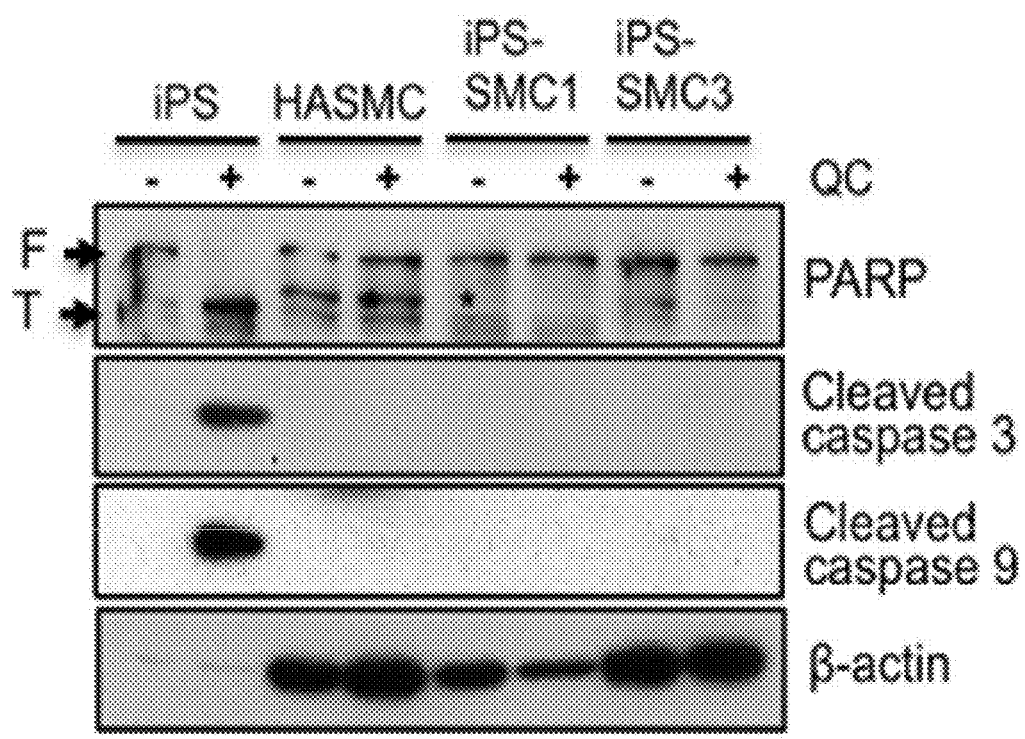
FIG. 1b shows the results of confirming the apoptosis marker proteins by a cell lysate, treated according to the same method as in FIG. 1a, using an immunoblotting method. As a result, the human induced pluripotent stem cells treated with quercetin exhibited the expression of Parp-1 cleavage (T type), cleavage types of caspase-3 and caspase-9 (cleaved caspase)

In order to confirm the functions of the differentiated cells which were completely differentiated into smooth muscle cells, an intracellular calcium reaction was used. As described in the reference article (Lee et al., 2006), intracellular or extracellular calcium transients were induced using pharmacological reagents, ATP or 75 mM $K^+$ solution, and the values were numerized in fluorescence using a calcium indicator Fura-2 (Molecular Probes, Eugene, Oreg.), and imaged.
Experimental Results
Apoptosis of Undifferentiated Human Induced Pluripotent Stem Cells by Quercetin and Confirmation of Human Induced Pluripotent Stem Cells-Derived Smooth Muscle Cells (iPS-SMC)
Apoptosis by Quercetin In order to confirm the selective apoptosis of undifferentiated human induced pluripotent stem cells by quercetin, human induced pluripotent stem cells (iPS) derived from human aortic smooth muscle cells (HASMC), HASMC, smooth muscle cell no. 1 differentiated-derived from iPS (iPS-SMC-1), and smooth muscle cell no. 3 differentiated-derived from iPS were treated with 50 μM quercetin for 24 hours, and apoptosis-specific phenotypic cell types were examined, as a result, a distinctive apoptosis-specific phenotypic cell type was discovered in the human induced pluripotent stem cells treated with quercetin (FIG. 1a). Additionally, when apoptosis-associated marker proteins were examined via immunoblotting assay, cleavage of Parp-1 (T type), cleavage types of caspase-3 and caspase-9 (cleaved caspase), which occur at the time of apoptosis, were expressed (FIG. 1b).

Figure 2A:
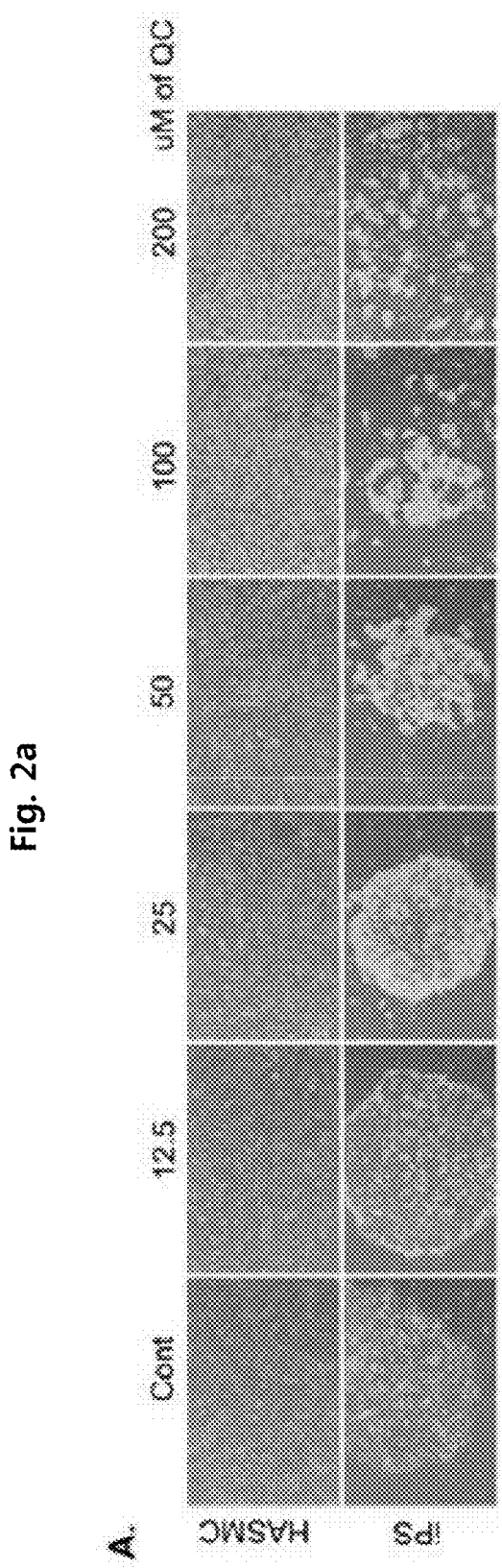
FIG. 2a shows the images of the degree of apoptosis in an apoptosis-specific cell phenotype of concentration-dependent pluripotent induced stem cells observed under microscope, after treating them with various concentrations of quercetin (QC).
Figure 2B:
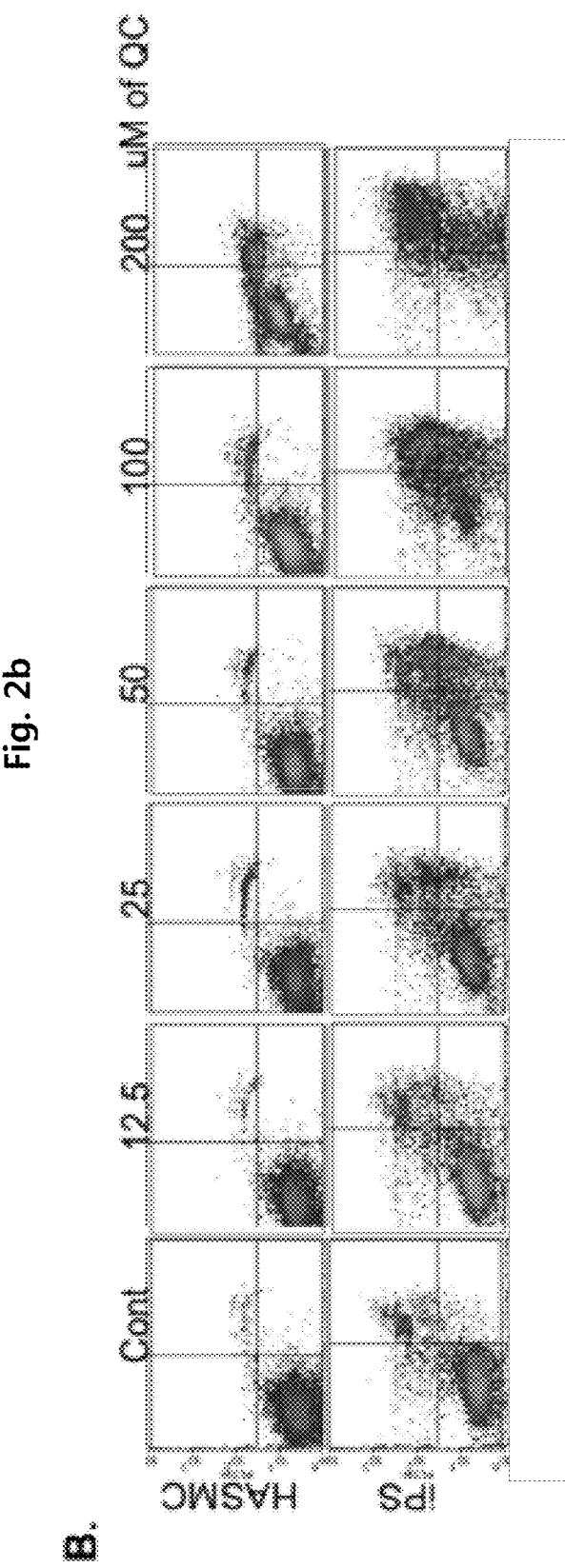
FIG. 2b shows the results of the degree of apoptosis of iPS and HASMC treated with various concentrations of quercetin in FIG. 2a, confirmed by Annexin V method.
Figure 2C:
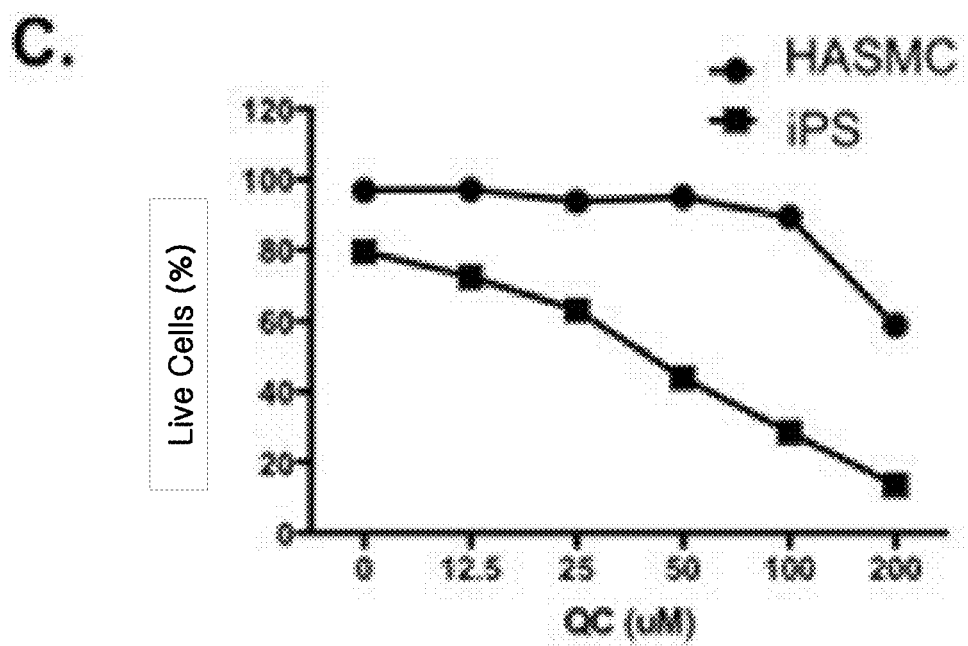
FIG. 2c is a graph showing the results of the degree of apoptosis obtained in FIG. 2b, wherein the rate of live cells in each of iPS and HASMC.

When treated with various concentrations of quercetin (QC) the degree of apoptosis of concentration-dependent induced pluripotent stem cells were confirmed in an apoptosis-specific phenotypic cell type (FIG. 2a). Additionally, the degree of apoptosis of iPS and HASMC by various concentrations of quercetin was confirmed via Annexin V method, and the results are shown in graphs, and the ratio of the respective live cells of iPS and HASMC were confirmed (FIGS. 2b and 2c).

Confirmation of Functions of Human Induced Pluripotent Stem Cells-Derived Smooth Muscle Cells (iPS-SMC)

Figure 3A:
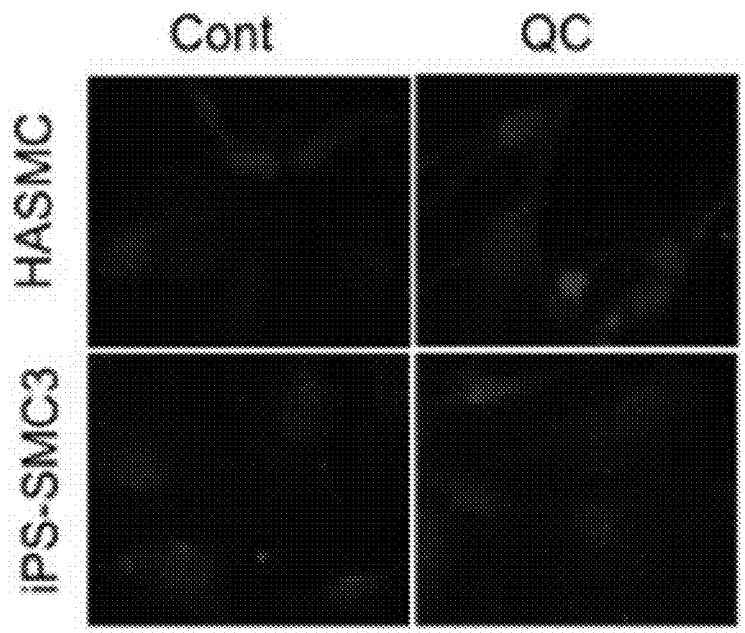
FIG. 3a shows the results of expression of α-Smooth muscle actin (α-SMA), which is known to specifically express in smooth muscle cells, confirmed by immunofluorescence method, after treating HASMC and iPS-SMC3 with 50 μM quercetin for 24 hours.
Figure 3B:
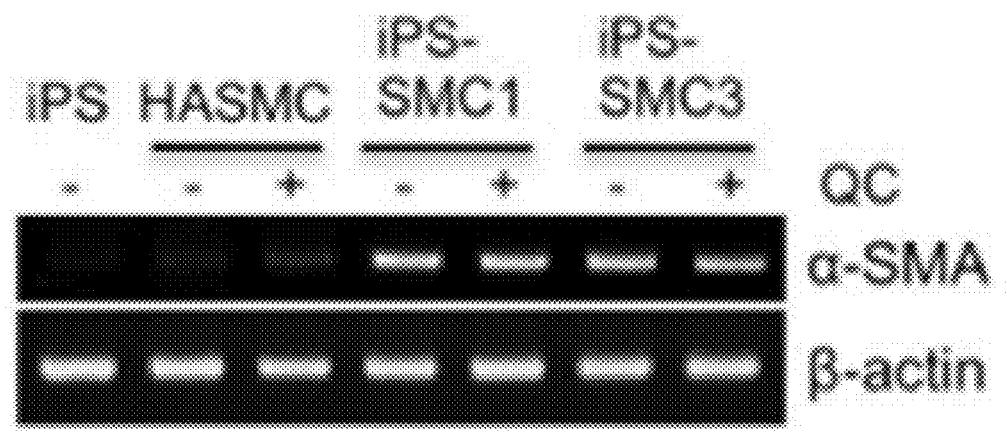
FIG. 3b shows the results of mRNA expression level of intracellular α-SMA of iPS-SMC1 and iPS-SMC3, treated by the same method as in FIG. 3a, confirmed by RT-PCR.

In order to confirm the functions of smooth muscle cells differentiated-derived from human induced pluripotent stem cells, HASMC and iPS-SMC3 were treated with 50 μM quercetin for 24 hours, and examined the expression of α-Smooth muscle actin (α-SMA), which is known to be specifically expressed in smooth muscle cells, via immuno fluorescence method, and as a result, the expression of α-SMA was confirmed. Additionally, the expression of α-SMA mRNA in the cells of iPS-SMC1 and iPS-SMC3 was confirmed via RT-PCR (FIGS. 3a and 3b).

Figure 3C:
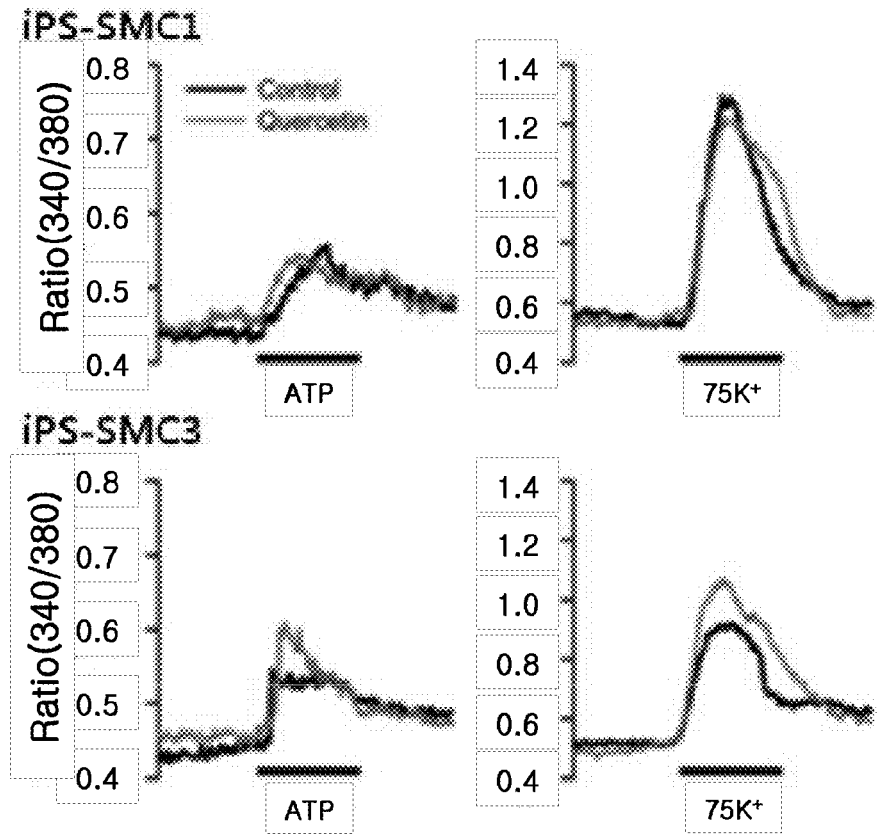
FIG. 3c shows the results of smooth muscle cells differentiated-derived from human induced pluripotent stem cells by measuring the intracellular calcium concentration of iPS-SMC1 and iPS-SMC3, after treating iPS-SMC1 and iPS-SMC3 with 50 μM quercetin or DMSO for 24 hours, followed by treating with ATP or 75 mM potassium solution ($75K^+$).
Figure 3D:
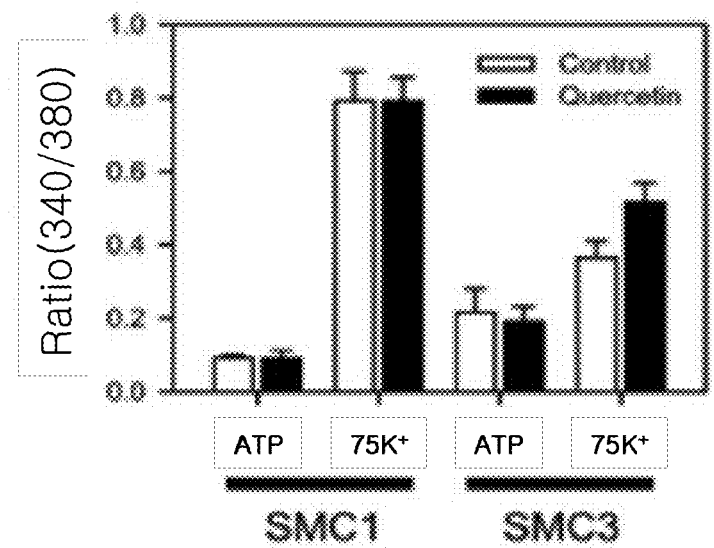
FIG. 3d is a graph showing the results of interior calcium concentrations measured in FIG. 3c.
Figure 4A:
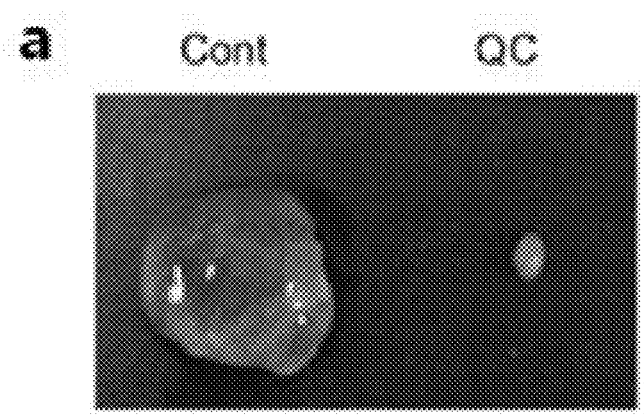
FIG. 4a shows the comparison result of teratoma formation capability between undifferentiated induced pluripotent stem cells, 10 weeks after treating them with 50 μM quercetin for 24 hours followed by injection into a mouse testis, and control group.
Figure 4B:
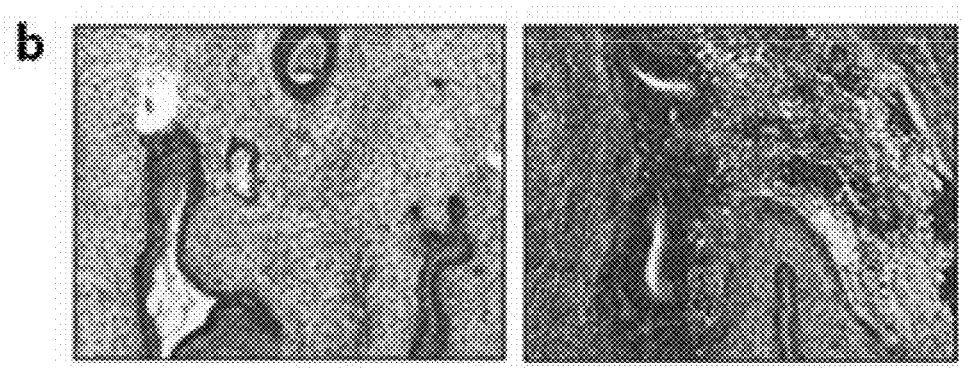

Additionally, in order to confirm the functions of smooth muscle cells differentiated-derived from human induced pluripotent stem cells, iPS-SMC1 and iPS-SMC3 were treated with 50 μM quercetin or DMSO for 24 hours, followed by treatment with ATP or 75 mM potassium solution (75K$^+$), and measured the concentration of intracellular calcium of iPS-SMC1 and iPS-SMC3, and thereby confirmed the functions as smooth muscle cells (FIGS. 3c and 3d).

Teratoma Forming Ability

In order to confirm the teratoma formation when treated with quercetin, undifferentiated induced pluripotent stem cells treated with 50 μM quercetin for 24 hours were injected into testis, and in 10 weeks thereafter, their teratoma forming ability was compared with the control group (induced pluripotent stem cells not treated with quercetin). As a result, secretory eipthelium and neural rosette structure were observed in the control group, and they were respectively stained with PAS stain and H&E stain, thereby confirming teratoma formation.

Apoptosis of Undifferentiated Human Induced Pluripotent Stem Cells by YM-155 and Confirmation of Human Induced Pluripotent Stem Cells-Derived Smooth Muscle Cells (iPS-SMC)

Apoptosis by YM-155

Figure 5:
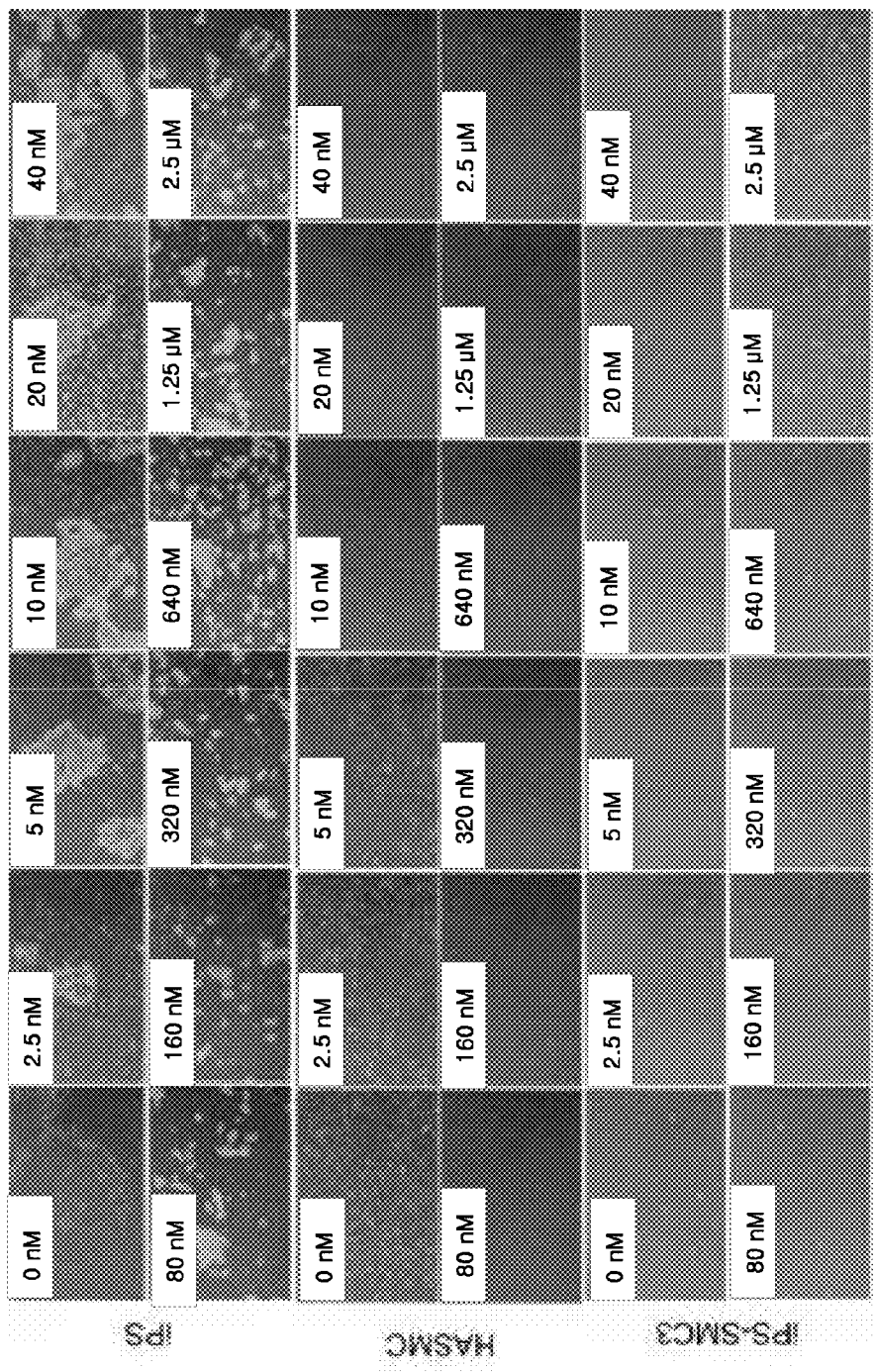
FIG. 5 shows the images of the degree of apoptosis in an apoptosis-specific cell type of iPS, HASMC, and iPS-SMC-3, after treating them with various concentrations of YM-155 for 24 hours, confirmed by microscope. As a result, the human induced pluripotent stem cells treated with YM-155 exhibited a distinct concentration-dependent apoptosis-specific phenotypic cell type.

In order to confirm the selective apoptosis of undifferentiated human induced pluripotent stem cells by YM-155, human induced pluripotent stem cells (iPS) derived from human aortic smooth muscle cells (HASMC), HASMC, and smooth muscle cell no. 3 differentiated-derived from iPS were treated with YM-155 for 24 hours, and apoptosis-specific phenotypic cell types were examined, as a result, a distinctive apoptosis-specific phenotypic cell type was discovered in the human induced pluripotent stem cells treated with concentration-dependent YM-155 (FIG. 5).

Figure 6A:
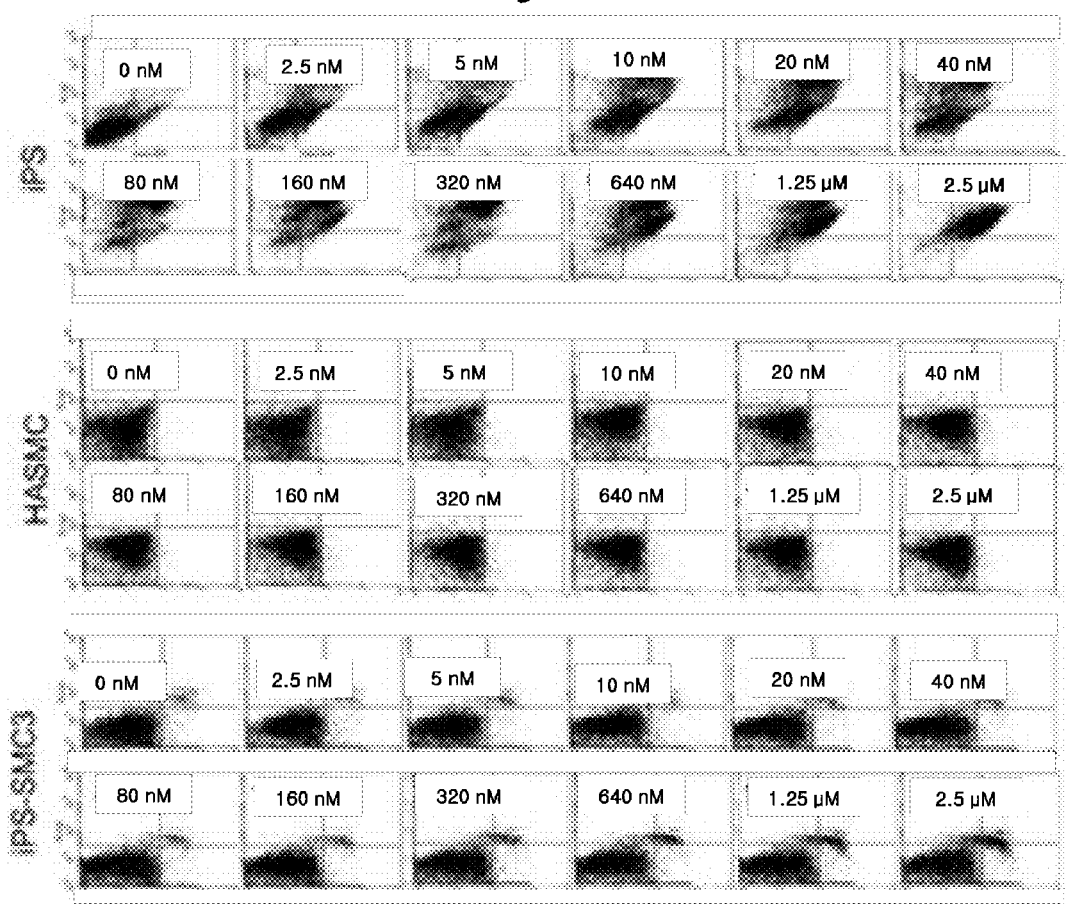
FIG. 6a shows the results of confirming the degree of apoptosis of concentration-dependent iPS, HASMC, and iPS-SMC3 by various YM-155 concentrations using Annexin V method, and measured by the FACS method.
Figure 6B:
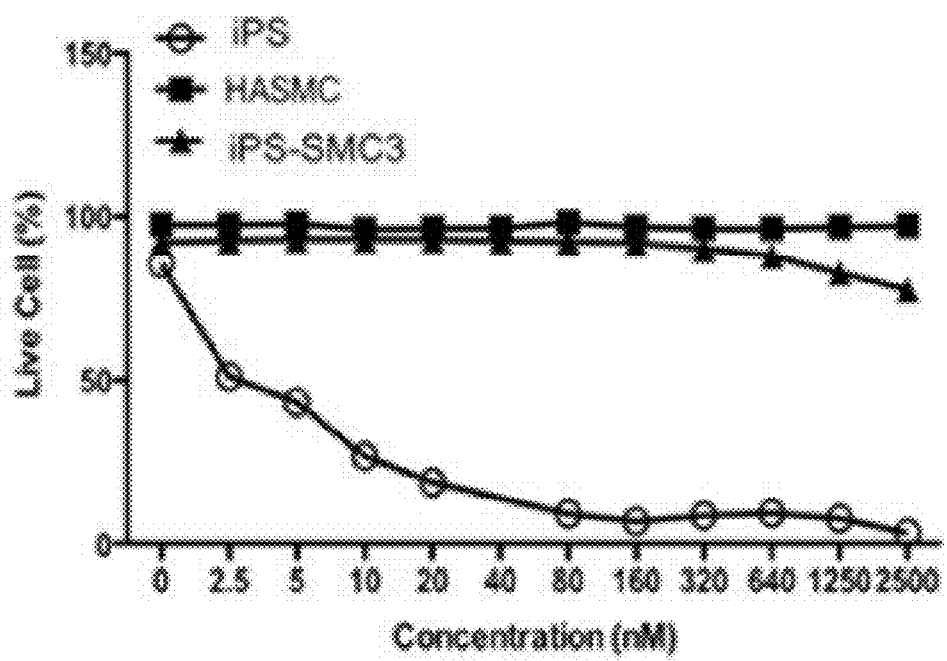
FIG. 6b is a graph showing the degree of apoptosis obtained in FIG. 6a, wherein the rate of live cells in each of iPS, HASMC, and iPS-SMC3.

Additionally, the degree of apoptosis of iPS, HASMC, and iPS-SMC3 by various concentrations of YM-155 was confirmed via Annexin V method, and the results are shown in graphs, and the ratio of the respective live cells of iPS, HASMC, and iPS-SMC3 were confirmed (FIGS. 6a and 6b).

Confirmation of Functions of Human Induced Pluripotent Stem Cells-Derived Smooth Muscle Cells (iPS-SMC)

Figure 7A:
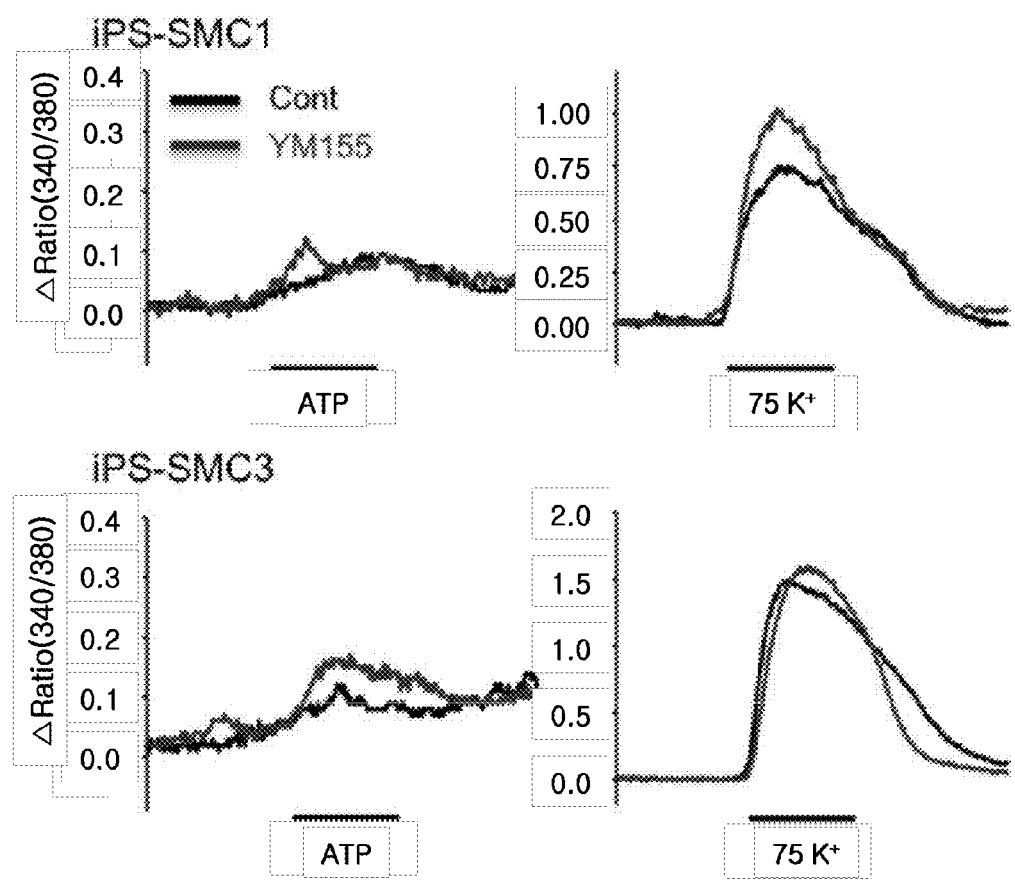
FIG. 7a shows the results of smooth muscle cells differentiated-derived from human induced pluripotent stem cells by measuring the intracellular calcium concentration of iPS-SMC1 and iPS-SMC3, after treating iPS-SMC1 and iPS-SMC3 with 50 nM YM-155 or DMSO for 24 hours, followed by treating with ATP or 75 mM potassium solution ($75K^+$).
Figure 7B:
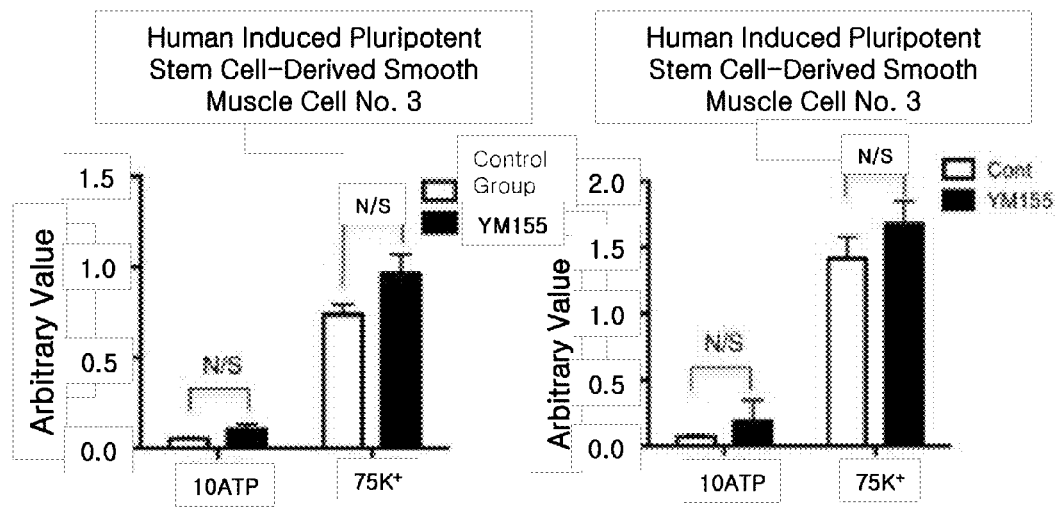

In order to confirm the functions of smooth muscle cells differentiated-derived from human induced pluripotent stem cells, iPS-SMC1 and iPS-SMC3 were treated with 50 nM YM-155 or DMSO for 24 hours, followed by treatment with ATP or mM potassium solution (75K$^+$), and measured the concentration of intracellular calcium of iPS-SMC1 and iPS-SMC3, and thereby confirmed the functions as smooth muscle cells (FIGS. 7a and 7b).

Figure 8A:
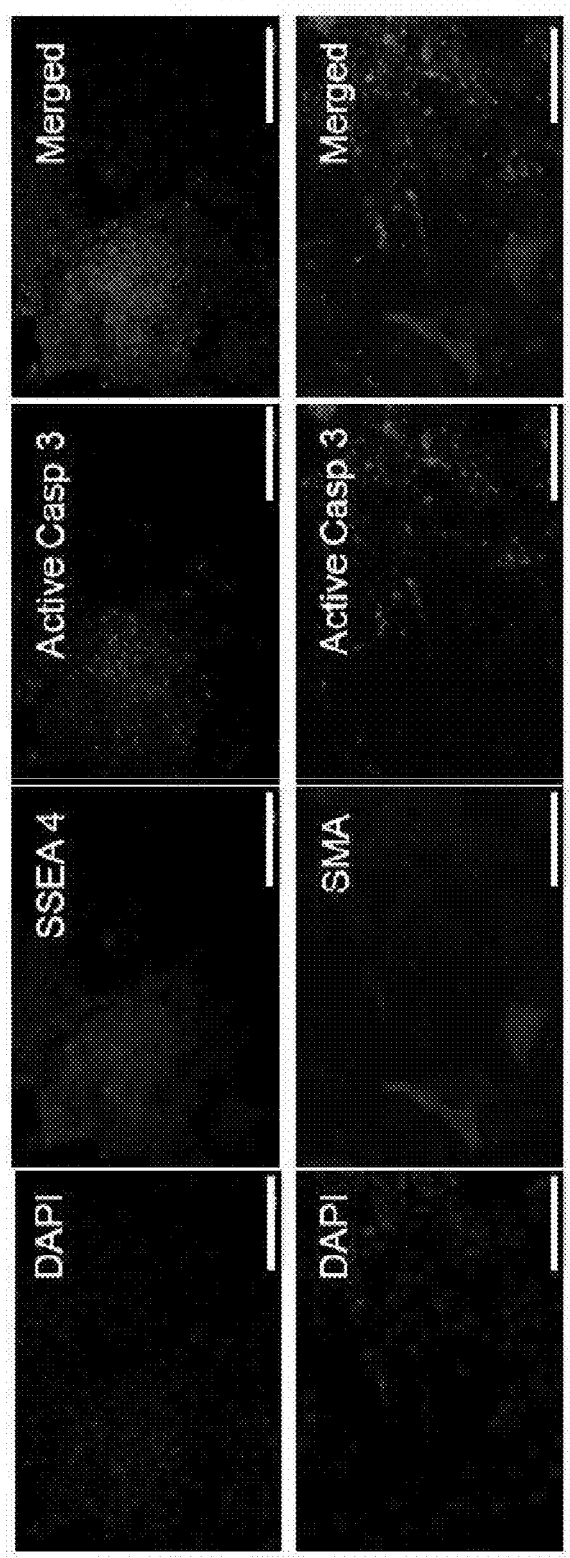
FIG. 8a shows the analysis results of immunostaining by SSEA-4 (green) and cleavage type-3 (red) (upper panel), or SMA (green) and cleavage type caspase-3 (red) (lower panel), after mixing human induced pluripotent stem cells and smooth muscle cells derived from human induced pluripotent stem cells (SMC3) at a 1:1 ratio, followed by treating with 50 μM quercetin for 24 hours. The scale bar denotes 100 μm.
Figure 8B:
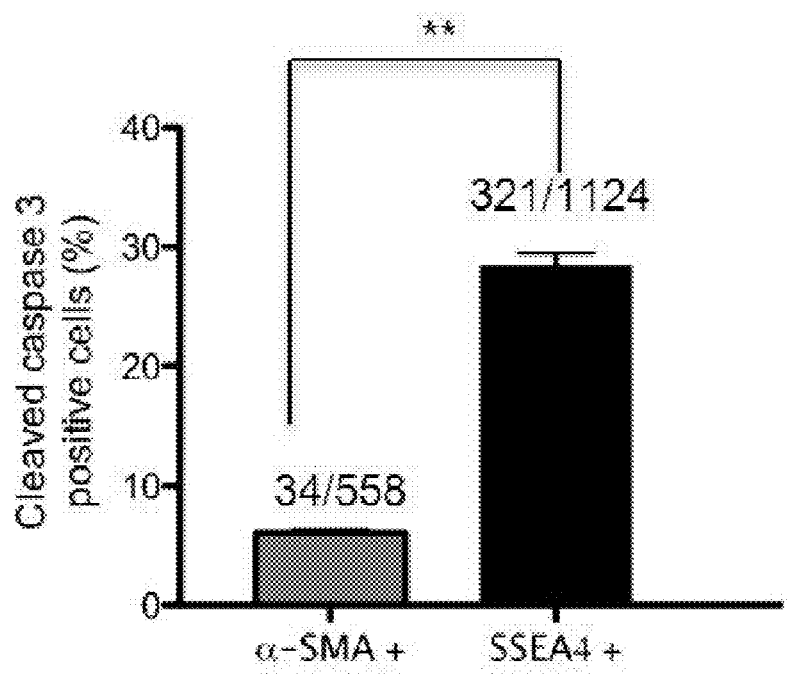
FIG. 8b shows a percentage of cleavage type caspase-3 positive population in SMA-positive population or SSEA-4-positive population. '**' denotes a significance of '$P<0.01$'.

Confirmation of the Effect of Quercetin Treatment on the Functions of Differentiated Cells In order to confirm the functions of smooth muscle cells differentiated-derived from human induced pluripotent stem cells, the population, which was cultured by mixing human induced pluripotent stem cells and the smooth muscle cells differentiated-derived from the human induced pluripotent stem cells in a 1:1 ratio, was treated with 50 μM quercetin for 24 hours, and examined the cleavage type caspase-3 positive population in the population of SMA-positive population or SSEA-4-positive population. As a result, the mixed cell population of human induced pluripotent stem cells-smooth muscle cells, after quercetin treatment, was shown to have an excellent cleavage type caspase-3 positive population within the SSEA-4 positive population (FIGS. 8a and 8b).

Figure 9A:
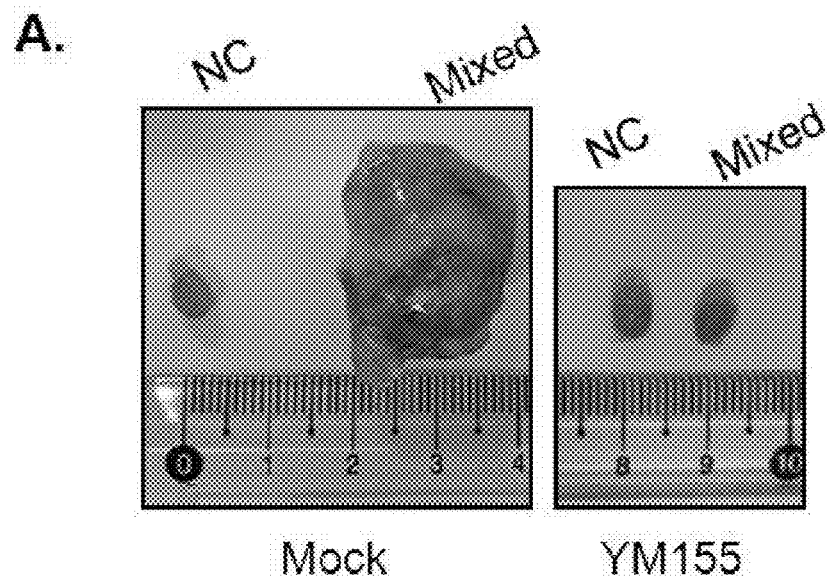
FIG. 9a shows the results of injection of a 1:1 mixture of human induced pluripotent stem cells and smooth muscle cells into a mouse. It shows the images of teratoma formed by injecting human induced pluripotent stem cells untreated or pretreated with 10 mM YM155 into a mouse. NC refers to a mouse testis into which cells were not injected.
Figure 9B:
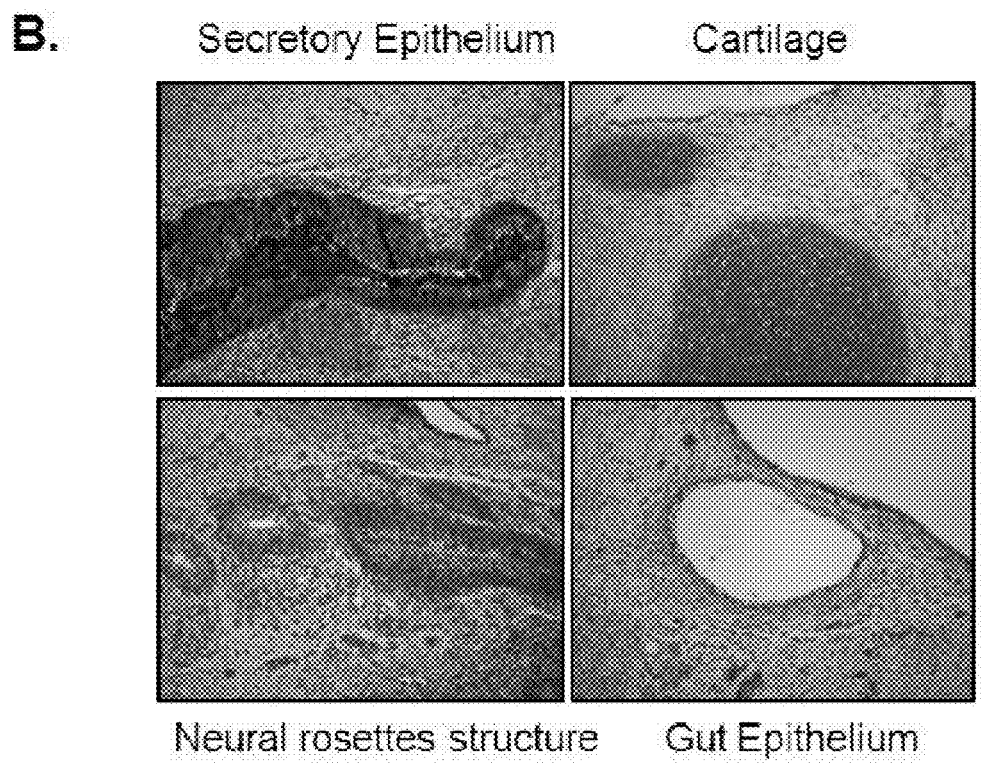
FIG. 9b shows the results of staining teratoma, formed in a mouse injected with human induced pluripotent stem cells, by H&E, Masson's trichrome, and Acian Blue staining. Teratoma produced intestinal epithelium, cartilage, secretory epithelium, and neural rosette structure.

Inducing Apoptosis of Human Induced Pluripotent Stem Cells by YM-155, a Survivin Inhibitor In order to confirm the selective apoptosis of human induced pluripotent stem cells by YM-155, a Survivin inhibitor, the result of injection of a 1:1 mixture of human induced pluripotent stem cells and smooth muscle cells is shown. Human induced pluripotent stem cells, either untreated or pretreated with 10 mM YM155, were injected into a mouse to induce teratoma (FIG. 9a). When the teratoma formed in the mouse injected with the human induced pluripotent stem cells was stained with H&E, Masson's trichrome, and Acian Blue, a single treatment with YM-155 for 24 hours was shown to inhibit teratoma formation.

The invention has been described in detail with reference to preferred embodiments thereof. However, it will be appreciated by those skilled in the art that the specific technical features are merely preferred embodiments of the present invention and they should not be construed as limiting the scope of the present invention, and thus the substantial scope of the present invention shall be defined in the appended claims and their equivalents

The invention claimed is:

1. A method for preparing a composition of differentiated cells derived from induced pluripotent stem cells (iPS), from which undifferentiated induced pluripotent stem cells have been removed, comprising:
   (a) preparing a cell sample including undifferentiated induced pluripotent stem cells and differentiated cells obtained by differentiating induced pluripotent stem cells; and
   (b) treating the cell sample of step (a) with quercetin of Formula 1 below or YM-155 of Formula 2 below, to cause selective apoptosis of the undifferentiated induced pluripotent stem cells of the cell sample:

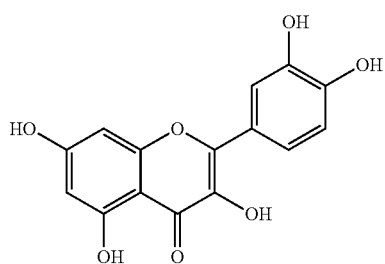

Formula 1

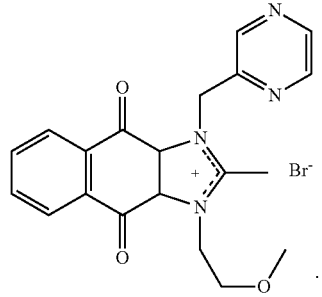

Formula 2

2. The method of claim 1, wherein the induced pluripotent stem cells are derived from humans, cattle, horses, goats, sheep, dogs, cats, mice, rats, or birds.

3. The method of claim 1, wherein the concentration of quercetin or YM-155 is in the range of 20 μM to 100 μM, or 2.5 nM to 80 nM, respectively.

4. A method for selective apoptosis of undifferentiated induced pluripotent stem cells, the method comprising contacting the cells with quercetin of Formula 1 below or YM-155 of Formula 2 below:

Formula 1
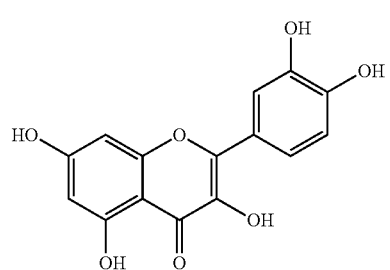
Formula 2
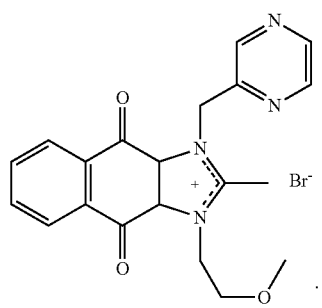
* * * * *

SEQUENCE LISTING

<160> NUMBER OF SEQ ID NOS: 4

<210> SEQ ID NO 1

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
gtcctctccc aagtccacac                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
gggagaccaa aagccttcat                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
agaacatggc atcatcacca                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
tacatggctg ggacattgaa                                              20
```